(12) United States Patent
Kawabata et al.

(10) Patent No.: US 8,273,907 B2
(45) Date of Patent: Sep. 25, 2012

(54) PROCESS FOR PRODUCING PROPYLENE OXIDE

(75) Inventors: Tomonori Kawabata, Toyonaka (JP); Hiroaki Abekawa, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 284 days.

(21) Appl. No.: 12/097,975

(22) PCT Filed: Dec. 25, 2006

(86) PCT No.: PCT/JP2006/325747
§ 371 (c)(1),
(2), (4) Date: Jun. 18, 2008

(87) PCT Pub. No.: WO2007/074760
PCT Pub. Date: Jul. 5, 2007

(65) Prior Publication Data
US 2009/0264665 A1 Oct. 22, 2009

(30) Foreign Application Priority Data

Dec. 26, 2005 (JP) ................................. 2005-371742
Aug. 31, 2006 (JP) ................................. 2006-235408

(51) Int. Cl.
*C07D 301/06* (2006.01)
(52) U.S. Cl. .................................................... 549/533
(58) Field of Classification Search .................. 549/533
See application file for complete search history.

(56) References Cited

U.S. PATENT DOCUMENTS

| | | | |
|---|---|---|---|
| 4,824,976 A | 4/1989 | Clerici et al. | |
| 6,498,259 B1 * | 12/2002 | Grey et al. ..................... | 549/533 |
| 7,326,401 B2 | 2/2008 | Tatsumi et al. | |
| 7,432,384 B2 * | 10/2008 | Le-Khac et al. ............... | 549/533 |
| 7,531,674 B2 * | 5/2009 | Ishino et al. ................... | 549/531 |
| 2003/0040649 A1 | 2/2003 | Oguchi et al. | |
| 2005/0014636 A1 | 1/2005 | Zhou et al. | |

FOREIGN PATENT DOCUMENTS

| | | |
|---|---|---|
| EP | 712852 A1 | 5/1996 |
| EP | 1 489 075 A1 | 12/2004 |
| EP | 1602651 A1 | 12/2005 |
| JP | 4-352771 A | 12/1992 |
| JP | 2002-511455 A | 4/2002 |
| JP | 2003-327425 A | 11/2003 |
| JP | 2004-269379 A | 9/2004 |
| JP | 2004-269380 A | 9/2004 |
| JP | 2005-508362 A | 3/2005 |
| JP | 2005-514364 A | 5/2005 |
| WO | WO-99/52885 A1 | 10/1999 |
| WO | WO-03/035632 A1 | 5/2003 |
| WO | WO-03/044001 A1 | 5/2003 |
| WO | WO-03/074506 A1 | 9/2003 |
| WO | WO-2004/078739 A1 | 9/2004 |

OTHER PUBLICATIONS

Heisei 14 Nendo Jisedai Kagaku Process Gijutsu Kaihatsu Non-halogen Kagaku Process Gijutsu Kaihatsu Seika Hokokusho, Heisei 15 Nen, "New Energy and Industrial Technology Development Organization," Itakusaki Japan Chemical Innovation Institute, 2003, pp. 152-180.
Heisei 13 Nendo Jisedai Kagaku Process Gijutsu Kaihatsu Non-halogen Kagaku Process Gijutsu Kaihatsu Seika Hokokusho, Heisei 15 Nen, "New Energy and Industrial Technology Development Organization," Itakusaki Japan Chemical Innovation Institute, 2003, pp. 168-210.
Wu et al., "Hydrothermal Synthesis of a Novel Titanosilicate with MWW Topology," Chemistry Letters, 2000, pp. 774-775.
Wu et al., "Preparation of B-free Ti-MWW through reversible structural conversion," Chem. Commun., 2002, pp. 1026-1027.
Ogura et al., "Effect of NH+4 Exchange on Hydrophobicity and Catalytic Properties of Al-Free Ti-Si-beta Zeolite," Journal of Catalysis, 2001, vol. 199, pp. 41-47.
Tuel., "Synthesis, characterization, and catalytic properties of the new TiZSM-12 zeolite," Zeolites, vol. 5, 1995, pp. 236-242.
Tuel., "Synthesis, characterization, and catalytic properties of titanium silicoaluminophosphate TAPSO-5," Zeolites, vol. 15, 1995, pp. 228-235.
Wu et al., "Hydroxylation of Aromatics with Hydrogen Peroxide over Titanosilicates with MOR and MFI Structures: Effect of Ti Peroxo Species on the Diffusion and Hydroxylation Activity," J. Phys. Chem. B, 1998, vol. 102, pp. 9297-9303.
Diaz-Cabañas et al., " Synthesis and catalytic activity of Ti-ITQ-7: a new oxidation catalyst with a three-dimensional system of large pore channels," Chem. Commun., 2000, pp. 761-762.
Balkus et al., "The synthesis of UTD-1, Ti-UTD-1 and Ti-UTD-8 using Cp*2 CoOH as a structure directing agent," Zeolites, 1995, vol. 15, pp. 519-525.
Koyano et al., "Synthesis of titanium-containing MCM-41," Microporous Materials, vol. 10, 1997, pp. 259-271.
Koyano et al., "Synthesis of titanium-containing mesoporous molecular sieves with a cubic structure," Chem. Commun., 1996, pp. 145-146. Wu et al., "Postsynthesis, Characterization, and Catalytic Properties in Alkene Epoxidation of Hydrothermally Stable Mesoporous Ti-SBA-15," Chem. Mater., 2002, vol. 14, pp. 1657-1664.
Rondinini et al., "Reference Value Standards and Primary Standards for pH Measurements in Organic Solvents and Water + Organic Solvent Mixtures of Moderate to High Permittivities," International Union of Pure and Applied Chemistry, 1987, vol. 59, No. 11, pp. 1549-1560.
Office Action mailed May 27, 2010 for Chinese application No. 200680049266.9.
Search Report mailed Jul. 15, 2010 for European Application No. 06843151.9.
Office Action in Chinese Application No. 200680049266.9 mailed Apr. 19, 2011, including an English translation.

* cited by examiner (Continued)

Primary Examiner — Taylor Victor Oh
(74) Attorney, Agent, or Firm — Birch, Stewart, Kolasch & Birch, LLP

(57) ABSTRACT

A process for more efficiently producing propylene oxide from propylene, oxygen, and hydrogen with catalysts which comprise a noble metal and a titanosilicate having pores not smaller than a 12-membered oxygen ring. The process for propylene oxide production is characterized by reacting propylene, oxygen, and hydrogen in a solution comprising water, a nitrite compound, and an ammonium salt in the presence of a noble metal catalyst and a titanosilicate catalyst having pores not smaller than a 12-membered oxygen ring.

6 Claims, No Drawings

PROCESS FOR PRODUCING PROPYLENE OXIDE

TECHNICAL FIELD

The present invention relates to a process for producing propylene oxide from propylene, oxygen, and hydrogen.

BACKGROUND ART

In a reaction for producing propylene oxide from hydrogen, oxygen and propylene by using palladium and TS-1 as catalysts, it has been reported that the amount of propylene oxide formed is increased and the amount of the by-product propane is reduced, when using water and methanol as solvents and adding ammonium hydroxide (see Patent Document 1, for example). Further, a method of a reaction for producing propylene oxide from hydrogen, oxygen, and propylene by using palladium and TS-1 as catalysts has been reported, wherein water and methanol are used as solvents and an ammonium hydrogencarbonate salt is added (Patent Document 2), or cesium phosphate is added to an aqueous solvent (Patent Document 3). In Patent Document 2 (paragraph [0008]) and Patent Document 3 (paragraph [00091]), there are such descriptions that titanium silicalite which is titanium zeolite having relatively small pores is preferable for oxidation of propylene, and that use of TS-1 titanium silicalite is absolutely advantageous. However, these methods are not necessarily satisfactory from the viewpoint of reaction efficiency.

Furthermore, a method for producing propylene oxide from hydrogen, oxygen and propylene has been reported, wherein Pd and a Ti-MWW catalyst or a catalyst containing a layered titanosilicate that is a precursor of Ti-MWW, each of which has pores of a 12-membered oxygen ring is used in an acetonitrile solvent (see non-Patent Document 1, for example). However, the efficiency is not necessarily satisfactory, either.

Patent Document 1: JP 2002-511455 A
Patent Document 2: JP 2005-514364 A
Patent Document 3: JP 2005-508362 A
Non-Patent Document 1: Next Generation Chemical Process Technological Development in 2002; Non-Halogen Chemical Process Technological Development Achievement Report; 152-180 (2003)

DISCLOSURE OF THE INVENTION

Problem to be Solved by the Invention

The present invention provides a process for more efficiently producing propylene oxide from propylene, oxygen, and hydrogen in the presence of catalysts which comprise a noble metal catalyst and a titanosilicate having pores not smaller than a 12-membered oxygen ring.

Means for Solving the Problem

That is, the present invention relates to a process for producing propylene oxide which comprises reacting propylene, oxygen, and hydrogen in a solution containing water, a nitrile compound, and an ammonium salt in the presence of a noble metal catalyst and a titanosilicate catalyst having pores not smaller than a 12-membered oxygen ring (hereinafter sometimes referred to as the titanosilicate of the present invention).

Effect of the Invention

According to the present invention, it is possible to efficiently produce propylene oxide from propylene, oxygen, and hydrogen.

BEST MODE FOR CARRYING OUT THE INVENTION

Typical examples of the noble metal catalyst to be used in the present invention include palladium, platinum, ruthenium, rhodium, iridium, osmium, gold, an alloy or a mixture thereof, and the like. Preferred noble metal catalysts include palladium, platinum, and gold. A more preferred noble metal catalyst is palladium.

Palladium can also be used as admixture with platinum, gold, rhodium, iridium, osmium, and the like. Among these, preferred metals for the admixture include platinum.

Usually, the noble metal catalyst supported on a carrier is used. The noble metal catalyst can be supported on the titanosilicate. Alternatively, it can be supported on a carrier other than the titanosilicate, such as an oxide such as silica, alumina, titania, zirconia, niobia, or the like, niobic acid, zirconium acid, tungsten acid, titanium acid, carbon, or a mixture thereof. When the noble metal catalyst is supported on a carrier other than the titanosilicate, the carrier supporting the noble metal catalyst can be mixed with the titanosilicate so as to use the mixture as a catalyst. Among the carriers other than the titanosilicate of the present invention, preferred one is carbon.

As a method for supporting the noble metal catalyst on a carrier, for example, illustrated is a method in which a noble metal colloidal solution obtained by dispersing noble metal particles using a dispersing agent such as citric acid, polyvinylalcohol, polyvinylpyrrolidone, sodium hexametaphosphate, or the like is supported on a carrier by impregnation or the like, followed by calcination under an inert gas atmosphere.

Alternatively, the noble metal catalyst can be prepared by supporting a noble metal compound as a noble metal source, a nitrate salt of a noble metal such as palladium nitrate, a sulfate salt such as palladium sulfate dihydrate, a halide of a noble metal such as palladium chloride, a palladium acetate carboxylic acid salt, or an ammine complex such as tetraamine palladium chloride hydrate or the like on a carrier by impregnation or the like, followed by reduction with a reducing agent. Also, the noble metal catalyst can be prepared by obtaining a hydroxide of a noble metal using an alkali such as sodium hydroxide, followed by reduction in a liquid phase or a gas phase with a reducing agent.

Examples of the reducing agent to be used in the case of reduction in a liquid phase include hydrogen, hydrazine monohydrate, formaldehyde, sodium borohydride, and the like. An alkali can be added in the case of using hydrazine monohydrate or formaldehyde.

Hydrogen can be used as a reducing agent for the reduction in a gas phase. The noble metal catalyst can be prepared by calcining and reducing the carrier supporting the noble metal source in the presence of a hydrogen gas. The temperature suitable for the reduction is varied depending on a noble metal source to be supported, but is usually 0° C. to 500° C.

On the other hand, the noble metal catalyst can be supported on a carrier by impregnation or the like using an ammine complex of a noble metal such as Pd tetraamine chloride, followed by reduction under an inert gas atmosphere with an ammonium gas generated during thermal decomposition. Although the reduction temperature is varied depending on the noble metal ammine complex, in the case of using Pd tetraamine chloride, the reduction temperature is usually 100° C. to 500° C., preferably 200° C. to 350° C. In any methods, if necessary, the thus-obtained catalyst can be activated by a heat treatment in an inert gas, an ammonium gas, vacuum, hydrogen, or air.

The thus-obtained noble metal catalyst-supporting material contains the noble metal catalyst usually in an amount ranging from 0.01 to 20 wt %, preferably from 0.1 to 5 wt %.

In the present specification, the pores in a titanosilicate having pores not smaller than a 12-membered oxygen ring means pores formed of an Si—O or Ti—O bond, and does not include pores between particles that are formed by primary particles.

The diameter of the titanosilicate pores is usually 0.6 to 1.0 nm in a crystalline titanosilicate and a layered titanosilicate and usually 2 to 10 nm in a mesoporous titanosilicate.

The composition of the titanosilicate is usually represented by the following formula (I):

$$x\mathrm{TiO_2 \cdot (1-x)SiO_2} \tag{I}$$

wherein x is usually 0.0001 to 0.5, preferably 0.01 to 0.2.

Usually, Ti of the titanosilicate is located inside of the SiO$_2$ skeleton and the titanosilicate has such a structure that a part of Si is replaced by Ti. Ti located inside of the SiO$_2$ skeleton is easily confirmed by a UV visible absorption spectrum, a titanium K-edge XAFS analysis or the like.

In general, the titanosilicate is synthesized by using a surfactant as a lubricant or a structure-directing agent, hydrolyzing a titanium compound and a silicon compound, and removing the surfactant by calcination or extraction, if necessary, after crystallization or improvement of pore regularity by hydrothermal synthesis or the like.

As a general preparation process for the crystalline titanosilicate having the Ti-MWW structure, processes disclosed in Chemistry Letters, 774-775 (2000), JP 2003-327425 A, Chemical Communications, 1026-1027 (2002), and the like are known. That is, a gel is prepared by hydrolyzing a silicon compound and a titanium compound in the presence of a structure-directing agent. The thus-obtained gel is subjected to a heat treatment in the presence of water by hydrothermal synthesis or the like to prepare a layered crystal precursor. The layered crystal precursor is crystallized by calcination, thereby obtaining a crystalline titanosilicate having an MWW structure.

Specific examples of the titanosilicate having pores not smaller than a 12-membered oxygen ring include crystalline titanosilicates such as Ti-Beta (e.g. Journal of Catalysis 199, 41-47 (2001)), Ti-ZSM-12 (e.g. Zeolites 15, 236-242 (1995)), TAPS0-5 (e.g. Zeolites 15, 228-235 (1995)), Ti-MOR (e.g. The Journal of Physical Chemistry B 102, 9297-9303 (1998)), Ti-ITQ-7 (e.g. Chemical Communications, 761-762 (2000)), Ti-UTD-1 (e.g. Zeolites 15, 519-525 (1995)) and Ti-MWW, a layered titanosilicate such as a Ti-MWW precursor, and mesoporous titanosilicates such as Ti-MCM-41 (e.g. Microporous Materials 10, 259-271 (1997)), Ti-MCM-48 (e.g. Chemical Communications 145-146 (1996)), Ti-SBA-15 (e.g. Chemistry of Materials 14, 1657-1664 (2002)), and the like. A preferred titanosilicate is Ti-MWW or a Ti-MWW precursor, and a more preferred titanosilicate is Ti-MWW.

The titanosilicate having pores not smaller than a 12-membered oxygen ring also includes a titanosilicate having pores not smaller than a 12-membered oxygen ring obtained by reacting a silylating agent, for example, 1,1,1,3,3,3-hexamethyldisilazane or the like with the titanosilicate. By the silylation, the activity or selectivity can be further improved, and the silylated titanosilicate (e.g. silylated Ti-MWW) obtained by the silylation can also be preferably used.

The titanosilicate can also be used after activation by a treatment with a hydrogen peroxide solution at an appropriate concentration. Usually, the concentration of the hydrogen peroxide solution is in the range of 0.0001 to 50 wt %. A solvent for the hydrogen peroxide solution is not particularly limited, but water or a solvent used in the propylene oxide synthesis reaction is preferred since it is convenient from the industrial viewpoint.

The weight ratio of the noble metal catalyst to the titanosilicate having pores not smaller than a 12-membered oxygen ring (noble metal catalyst weight/titanosilicate weight) is preferably 0.01 to 100 wt %, more preferably 0.1 to 20 wt %.

Examples of the nitrile compound include straight chain or branched chain saturated aliphatic nitrile or aromatic nitrile and the like. Examples of the nitrile compound include $C_2$-$C_4$ alkylnitrile such as acetonitrile, propionitrile, isobutylonitrile, butylonitrile, etc. and benzonitrile, among which acetonitrile is preferred. Usually, the ratio between water and the nitrile compound is 90:10 to 0.01:99.99, preferably 50:50 to 0.1:99.9 by weight. When the ratio of water is too large, propylene oxide tends to react with water to cause ring-opening deterioration, resulting in the lowering of the formation activity of propylene oxide. To the contrary, when the ratio of the nitrile compound is too large, a solvent recovery cost is increased.

As the ammonium salt, compounds represented by the following formula (II):

$$\mathrm{R_4NX} \tag{II}$$

wherein R's are the same or different and independently represent hydrogen, an alkyl group, or an aryl group, and X represents an anion of an acid, can be used.

Examples of the alkyl group include $C_{1-20}$ alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, and the like, and examples of the aryl group include a phenyl group, a naphthyl group, a pyridyl group, and the like.

Examples of the acid ion represented by X include inorganic acid ions such as a sulfate ion, a hydrogen sulfate ion, a carbonate ion, a hydrogencarbonate ion, a phosphate ion, a hydrogenphosphate ion, a dihydrogenphosphate ion, a hydrogenpyrophosphate ion, a pyrophosphate ion, a halogen ion, a nitrate ion, and the like, organic acid (e.g. carboxylic acid) ions, such as an acetate ion, and the like.

Examples of the ammonium of the formula (II) include ammonium salts of inorganic acids such as ammonium sulfate, ammonium hydrogensulfate, ammonium carbonate, ammonium hydrogencarbonate, diammonium hydrogenphosphate, ammonium dihydrogenphosphate, ammonium phosphate, ammonium hydrogenpyrophosphate, ammonium pyrophosphate, ammonium chloride, ammonium nitrate, and the like, ammonium salts of organic acids such as ammonium acetate, and the like. Preferred ammonium salts include ammonium dihydrogenphosphate.

Examples of the ammonium cation which forms the ammonium salt of the formula (II) include alkylammoniums, alkylarylammoniums, and the like.

Examples of the alkylammonium include tetramethylammonium, tetraethylammonium, tetra-n-propylammonium, tetra-n-butylammonium, cetyltrimethylammonium, and the like. Examples of the alkylammonium salt include a sulfate salt, a hydrogensulfate salt, a carbonate salt, a hydrogencarbonate salt, a hydrogenphosphate salt, a dihydrogenphosphate salt, a phosphate salt, a hydrogenpyrophosphate salt, a pyrophosphate salt, and a halide such as a chloride, and an acetate salt of these alkylammoniums, and the like.

The amount of the ammonium salt to be added is usually 0.001 to 100 mmol/kg relative to a unit solvent weight (total weight of water and the nitrile compound). The effect is hardly exhibited when the ammonium salt amount is too small, while there is a risk of increasing the possibility of clogging due to the ammonium salt depositing in a plant when the ammonium salt amount is too large.

The ammonium salt of the formula (II) to be used may be that formed in a reaction system by adding ammonium hydroxide or alkylammonium hydroxide to an acid composed of the anion of an acid represented by X and a proton, preferably the one among the acids usable as a buffer agent such as phosphoric acid, hydrogencarbonate, hydrogenphosphate, dihydrogenphosphate, hydrogenpyrophosphate, or pyrophosphoric acid, to the reaction system.

When a pH value of the solution becomes too high, sometimes, propylene oxide formation activity is lowered. On the other hand, when the pH value is too low, sometimes, the propylene oxide selectivity is lowered because the formation of propane byproduct is enhanced or propylene oxide formation activity is lowered. Further, propylene oxide selectivity is also lowered at a too high or a too low pH value because ring open deterioration of propylene oxide is caused by an acid or an alkali. Therefore, the solution having a pH value of 3.0 to 6.6 can be preferably used. More preferably, the solution having a pH value of 5.0 to 6.6 is used.

In the case of adjusting the pH of the solution to the preferred pH value, when it is difficult to adjust the pH value to the preferred value by addition of only one type of the ammonium salt to the solution, an acid, a base, a buffer agent, and the like can be used in combination with the ammonium salt. Further, in the case of adding a basic ammonium salt such as ammonium hydroxide, ammonium carbonate, ammonium hydrogencarbonate, or diammonium hydrogenphosphate, the pH value measured by a pH meter may exceed 6.6. In such a case, the pH value of the solution containing water, the nitrile compound, and the ammonium salt (a pH value of the solution measured by a pH meter) is adjusted to the preferable range of pH 3.0 to 6.6 or the more preferable range of pH 5.0 to 6.6 by further adding an acid, a buffer agent or the like.

In the case where an ammonium salt such as ammonium hydrogensulfate is added, a pH value measured by a pH meter may be lower than 5.0. In such a case, the pH value of the solution measured by the pH meter can also be adjusted to the more preferable range of pH 5.0 to 6.6 by further adding a base, a buffer agent, or the like.

Typically, the production process of the present invention is carried out by supplying the solution containing water, the nitrile compound, and the ammonium salt, of which the pH value measured by a pH meter is adjusted to the preferable range, to a reactor.

In the reaction of the present invention, when a pH value of the solution is measured in the reaction system, it may be varied depending on conditions because the reaction is sometimes carried out under pressurized pressure or at a high temperature. However, the pH value in the process of the present invention means a value obtained by measuring the pH of the solution prepared for supplying to the reaction system with a pH meter at 20° C. to 25° C.

A method for measuring the pH value with a pH meter in the present invention is usually in accordance with the following method.

To start with, a double junction sleeve type comparison electrode is used as a comparison electrode. Next, a KCl solution of an outer column solution of the comparison electrode, for which water is generally used as a solvent, is changed to a test liquid in the same manner as described in the pH measurement method in an organic solvent system that is recommended by IUPAC [see Pure and Applied Chemistry 59, 1549-1560 (1987)]. At this time, 0.05 mol/kg of potassium hydrogenphthalate is preliminarily added as a buffer to the KCl solution of the solvent used for the measurement in the same manner as in the method of IUPAC. A saturated solution is usually used as the KCl solution. By measuring the pH with the use of the comparison electrode, the pH of the present invention can be measured with a pH meter. Since the pH value of the present invention measured with a pH meter means the pH value measured at 20° C. to 25° C., the measurement is carried out at a measurement temperature of 20° C. to 25° C.

The pH value measured with a pH meter is usually obtained from a value obtained by measuring a liquid junction electromotive force by using a reference electrode and a comparison electrode. However, it is sometimes necessary to calibrate the pH value due to an inclination different from a logical value and generation of an asymmetric potential difference in practice. The calibration is generally carried out in an aqueous solvent, and the measurement is also carried out in an aqueous solvent. However, in the case where an organic solvent is mixed, it is recommendable to carry out the calibration every time the composition of the solvent is changed in order to obtain a more accurate pH value. Nevertheless, since to carry out the calibration every time the liquid to be measured is changed is complicated, a pH value measured after the calibration in an aqueous solution with a pH meter is used in the present invention.

As a reaction method for the reaction according to the present invention, a circulation type fixed bed reaction, a circulation type complete slurry mixing reaction, and the like can be employed.

Usually, a partial pressure ratio between oxygen and hydrogen supplied to the reactor is in the range of 1:50 to 50:1. The preferred partial pressure ratio between oxygen and hydrogen is 1:2 to 10:1. In any ranges, it is preferable to keep the partial pressure ratio outside the explosion range from the viewpoint of safety. Sometimes, the formation rate of propylene oxide may be lowered when the partial pressure ratio between oxygen and hydrogen (oxygen/hydrogen) is too high. Further, the propylene oxide selectivity may be lowered due to the increase in the formation of propane by-product when the partial pressure ratio between oxygen and hydrogen (oxygen/hydrogen) is too low.

The oxygen and the hydrogen gas to be used in the reaction can be diluted with a dilution gas. Examples of the dilution gas include a nitrogen gas, an argon gas, a carbon dioxide gas, a methane gas, an ethane gas, a propane gas, and the like. Although the concentration of the dilution gas is not particularly limited, if necessary, oxygen and hydrogen is diluted.

As the oxygen, an oxygen gas or molecular oxygen such as the air can be used. As the oxygen gas, an oxygen gas produced by a low cost pressure swing method can be used, and a high purity oxygen gas produced by cryogenic separation or the like can also be used, if necessary.

The reaction temperature is usually 0° C. to 150° C., preferably 40° C. to 90° C. The reaction speed is lowered when the reaction temperature is too low, while a by-product due to a side reaction may be increased when the reaction temperature is too high.

The reaction pressure is not particularly limited, but the reaction pressure is usually be 0.1 to 20 MPa, preferably 1 to 10 MPa, by a gauge pressure. When the reaction pressure is too low, dissolution of the raw material gas may become insufficient, which results in a lower reaction rate, while costs for reaction facilities may be increased when the reaction pressure is too high.

After the reaction, the liquid phase or the gas phase withdrawn from the reactor is separated by distillation to obtain the objective product.

Hereinafter, the present invention will be illustrated by Examples, but the present invention is not limited to Examples.

Example 1

Ti-MWW used was prepared in accordance with the method described in Chemistry Letters, 774-775 (2000).

A gel composed of 9.1 kg of piperidine, 25.6 kg of purified water, 6.2 kg of boric acid, 0.54 kg of TBOT (tetra-n-butylorthotitanate), and 4.5 kg of fumed silica (cab-o-sil M7D) was prepared with stirring at room temperature under an atmosphere of air in an autoclave, followed by aging for 1.5 hours and then sealing. After raising the temperature over 10 hours with stirring, hydrothermal synthesis was carried out by maintaining at a temperature of 170° C. for 168 hours to obtain a suspension. The suspension was filtered and washed until a pH value of the filtrate became about 10. Then, the filter cake was dried at 50° C. to obtain white powder still containing moisture. To 350 g of the powder was added 3.5 L of 13 wt % nitric acid, followed by refluxing for 20 hours. Then, the refluxed mixture was filtered and washed until the pH of the mixture became about neutral, followed by drying at 50° C. to obtain 98 q of sufficiently dried white powder. The X ray diffraction pattern of the white power was measured by using an X ray diffraction apparatus using copper K-α radiation to confirm that the white powder was a Ti-MWW precursor. The thus-obtained Ti-MWW was calcined at 530° C. for 6 hours to obtain a Ti-MWW powder. The MWW structure of the thus-obtained powder was confirmed by measurement of an X ray diffraction pattern, and the titanium content determined by an TCP emission analysis was 0.9 wt %.

Further, a Pd/carbon black (CB) catalyst used in the reaction was prepared in accordance with the method described in US 2005-0014636 A. In a 500 mL-eggplant shaped flask, 0.56 mmol of palladium chloride, 0.006 mmol of platinum chloride, sodium polyacrylate (molecular weight: 1200, 1.27 mmol), and 500 mL of an aqueous solution containing 30 mmol of hydrogen chloride were mixed, followed by stirring for 1 hour at room temperature under an atmosphere of air. A hydrogen gas was introduced into the mixture at a feed rate of 100 mL/min at room temperature for 20 minutes to form a Pd colloid. To the colloidal solution, 6 g of a commercially available CB (SEAST 9, a product of Tokai Carbon Co., Ltd.) was added, followed by stirring for 8 hours. After the stirring, moisture was removed by using a rotary evaporator, followed by vacuum drying at 50° C. for 12 hours. The thus-obtained precursor powder was calcined under a nitrogen atmosphere at 300° C. for 6 hours to obtain Pd/CB. The palladium content and the platinum content confirmed by an ICP emission analysis were 1.01 wt % and 0.02 wt %, respectively.

The reaction was carried out by using an autoclave having a capacity of 0.5 L as a reactor. A raw material gas having a propylene/oxygen/hydrogen/nitrogen volume ratio of 4/1/8/87 was supplied at a feed rate of 16 L/hr, and a solution having a water/acetonitrile ratio of 20/80 (by weight) and containing 0.7 mmol/kg of ammonium dihydrogenphosphate (the pH value measured with a pH meter: 6.05) was supplied at a feed rate of 108 mL/hr. By separating a liquid phase of the reaction mixture from the reactor via a filter, a continuous reaction was carried out under the conditions of a temperature of 60° C., pressure of 0.8 MPa (gauge pressure) and a residence time of 90 minutes. During the reaction, 131 g of the reaction solvent, 0.133 g of Ti-MWW, 0.03 g of Pd/CB were retained in the reaction mixture in the reactor. A liquid phase and a gas phase withdrawn 5 hours after the initiation of the reaction were analyzed by gas chromatography to confirm that: propylene oxide formation activity per unit Ti-MWW weight was 3.28 mmol-PO/g-Ti-MWW·h; the selectivity based on propylene was 72%; and the selectivity based on hydrogen (formed propylene oxide molar amount/consumed hydrogen molar amount) was 35%.

Example 2

In a similar manner as that of Example 1, the reaction was carried out except that 0.6 g of the Ti-MWW powder obtained in Example 1 was treated with 100 g of a solution having a water/acetonitrile ratio of 20/80 (by weight) and containing 0.1 wt % of hydrogen peroxide at room temperature for 1 hour, followed by washing with 500 mL of water and filtration, and the thus-obtained substance was used for the reaction; and that the reaction was carried out by using a water/acetonitrile (20/80) solution containing 0.7 mmol/kg of ammonium nitrate (a pH value measured with a pH meter: 5.50) in place of the water/acetonitrile (20/80) solution containing 0.7 mmol/kg of ammonium dihydrogenphosphate. A liquid phase and a gas phase withdrawn 5 hours after the initiation of the reaction were analyzed by gas chromatography to confirm that: propylene oxide formation activity per unit Ti-MWW weight was 2.64 mmol-PO/g-Ti-MWW·h; the selectivity based on propylene was 67%; and the selectivity based on hydrogen was 23%.

Example 3

In a similar manner as that in Example 2, the reaction was carried out except that a water/acetonitrile (20/80) solution containing 0.7 mmol/kg of ammonium hydrogen sulfate (a pH value measured with a pH meter: 3.37) was used in place of the water/acetonitrile (20/80) solution containing 0.7 mmol/kg of ammonium nitrate. A liquid phase and a gas phase withdrawn 5 hours after the start of the reaction were analyzed by gas chromatography to confirm that: propylene oxide formation activity per unit Ti-MWW weight was 2.44 mmol-PO/g-Ti-MWW·h; the selectivity based on propylene was 61%; and the selectivity based on hydrogen was 19%.

Comparative Example 1

In a similar manner as that in Example 1, the reaction was carried out except that a water/methanol (22/78) solution containing 6.3 mmol/kg of ammonium hydroxide was used in place of the water/acetonitrile (20/80) solution containing 0.7 mmol/kg of ammonium dihydrogenphosphate and TS-1 containing 1.3 wt % of titanium was used in place of Ti-MWW. A liquid phase and a gas phase withdrawn 5 hours after the initiation of the reaction were analyzed by gas chromatography to confirm that: propylene oxide formation activity per unit TS-1 weight was 0.03 mmol-PO/g-TS-1·h; the selectivity based on propylene was 7%; and the selectivity based on hydrogen was 6%.

Comparative Example 2

In a similar manner as that in Example 1, the reaction was carried out except that a water/acetonitrile (20/80) solution containing no additive (a pH value measured with a pH meter: 6.75) was used in place of the water/acetonitrile (20/80) solution containing 0.7 mmol/kg of ammonium dihydrogenphosphate. A liquid phase and a gas phase withdrawn 5 hours after the initiation of the reaction were analyzed by gas chromatography to confirm that: propylene oxide formation activity per unit Ti-MWW weight was 1.02 mmol-PO/g-Ti-MWW·h; the selectivity based on propylene was 50%; and the selectivity based on hydrogen was 11%.

INDUSTRIAL APPLICABILITY

As described hereinabove, according to the present invention, it is possible to provide a process for more efficiently producing propylene oxide from propylene, oxygen, and hydrogen by using catalysts containing a noble metal and a titanosilicate having pores not smaller than a 12-membered oxygen ring.

The invention claimed is:

1. A process for producing propylene oxide which comprises reacting propylene, oxygen, and hydrogen in a solution containing water, acetonitrile, and an ammonium salt in the presence of a noble metal catalyst and a titanosilicate catalyst having pores not smaller than a 12-membered oxygen ring.

2. The process according to claim 1, wherein the solution containing water, acetonitrile, and an ammonium salt has a pH value of 3.0 to 6.6.

3. The process according to claim 1, wherein the solution containing water, acetonitrile, and an ammonium salt has a pH value of 5.0 to 6.6.

4. The process according to claim 1, wherein the ammonium salt is ammonium dihydrogenphosphate.

5. The process according to claim 1, wherein the noble metal catalyst is palladium.

6. The process according to claim 1, wherein the titanosilicate having pores not smaller than a 12-membered oxygen ring is Ti-MWW, a Ti-MWW precursor, or silylated Ti-MWW.

* * * * *